(12) United States Patent
Unger

(10) Patent No.: US 8,968,306 B2
(45) Date of Patent: Mar. 3, 2015

(54) SURGICAL FORCEPS

(75) Inventor: Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 837 days.

(21) Appl. No.: 13/205,999

(22) Filed: Aug. 9, 2011

(65) Prior Publication Data

US 2013/0041370 A1    Feb. 14, 2013

(51) Int. Cl.
| | |
|---|---|
| *A61B 18/12* | (2006.01) |
| *A61B 17/28* | (2006.01) |
| *A61B 17/3211* | (2006.01) |
| *A61B 18/14* | (2006.01) |
| *A61B 17/3205* | (2006.01) |
| *A61B 18/00* | (2006.01) |

(52) U.S. Cl.
CPC ......... *A61B 17/2816* (2013.01); *A61B 17/3211* (2013.01); *A61B 18/1442* (2013.01); *A61B 17/32053* (2013.01); *A61B 2018/00404* (2013.01); *A61B 2018/0063* (2013.01); *A61B 2018/1452* (2013.01); *A61B 2018/1495* (2013.01); *A61B 2018/1455* (2013.01)
USPC .............................................. 606/51; 606/52

(58) Field of Classification Search
CPC ........... A61B 17/2816; A61B 18/1442; A61B 2018/1452; A61B 2018/1455; A61B 2018/1495
USPC ............. 606/27, 34, 41, 48–52, 174; 277/376
See application file for complete search history.

(56) References Cited

U.S. PATENT DOCUMENTS

| | | | |
|---|---|---|---|
| 2,619,965 A | * | 12/1952 | Goldstone ..................... 606/118 |
| 2,632,661 A | | 3/1953 | Cristofv |
| 3,302,648 A | * | 2/1967 | Nelson .......................... 606/158 |
| D249,549 S | | 9/1978 | Pike |
| D263,020 S | | 2/1982 | Rau, III |
| D295,893 S | | 5/1988 | Sharkany et al. |
| D295,894 S | | 5/1988 | Sharkany et al. |
| D298,353 S | | 11/1988 | Manno |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

Int'l Search Report EP 11 006233.8 dated Feb. 2, 2012.

(Continued)

*Primary Examiner* — Michael Peffley
*Assistant Examiner* — Daniel Fowler

(57) ABSTRACT

A forceps includes a disposable shaft and a reusable shaft. The shafts each including a jaw member disposed at a distal end thereof. The shafts are releasably coupled to one another about a pivot and are moveable relative to one another for moving the jaw members between an open position and a closed position. The disposable shaft includes a first tissue sealing plate disposed thereon and an electrical, connector coupled thereto that includes a plurality of wires extending therethrough and into the disposable shaft member. One or more wires is coupled to the first tissue sealing plate and one or more wires is coupled to a second tissue sealing plate that is configured for releasable engagement with the jaw member of the reusable shaft member. The tissue sealing plates are adapted to conduct energy through tissue for sealing tissue grasped between the jaw members.

12 Claims, 8 Drawing Sheets

(56) References Cited

U.S. PATENT DOCUMENTS

| | | | |
|---|---|---|---|
| D299,413 S | 1/1989 | DeCarolis | |
| 4,914,820 A * | 4/1990 | Saito | 30/254 |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| 5,951,549 A * | 9/1999 | Richardson et al. | 606/45 |
| D416,089 S | 11/1999 | Barton et al. | |
| 6,050,996 A * | 4/2000 | Schmaltz et al. | 606/51 |
| D424,694 S | 5/2000 | Tetzlaff et al. | |
| D425,201 S | 5/2000 | Tetzlaff et al. | |
| H1904 H | 10/2000 | Yates et al. | |
| 6,277,117 B1 | 8/2001 | Tetzlaff et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,041,102 B2 * | 5/2006 | Truckai et al. | 606/51 |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| 7,179,258 B2 | 2/2007 | Buysse et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| 7,318,725 B2 * | 1/2008 | Zepf | 433/159 |
| D564,662 S | 3/2008 | Moses et al. | |
| D567,943 S | 4/2008 | Moses et al. | |
| 7,393,348 B2 * | 7/2008 | Dworschak et al. | 606/1 |
| D575,395 S | 8/2008 | Hushka | |
| D575,401 S | 8/2008 | Hixson et al. | |
| D582,038 S | 12/2008 | Swoyer et al. | |
| 7,641,653 B2 | 1/2010 | Dalla Betta et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 8,152,834 B2 * | 4/2012 | McGarity et al. | 606/205 |
| D661,394 S | 6/2012 | Romero et al. | |
| 2002/0188294 A1 * | 12/2002 | Couture et al. | 606/51 |
| 2003/0109875 A1 | 6/2003 | Tetzlaff et al. | |
| 2003/0171747 A1 * | 9/2003 | Kanehira et al. | 606/45 |
| 2005/0119655 A1 | 6/2005 | Moses et al. | |
| 2006/0167452 A1 | 7/2006 | Moses et al. | |
| 2007/0260241 A1 | 11/2007 | Dalla Betta et al. | |
| 2009/0255130 A1 * | 10/2009 | Jalmberger | 30/266 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244098 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011152195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2006/021269 A1 | 3/2006 |

(56) References Cited

FOREIGN PATENT DOCUMENTS

| WO | 2005110264 A3 | 4/2006 |
|---|---|---|
| WO | 2008/040483 A1 | 4/2008 |
| WO | 2011068795 A1 | 6/2011 |

OTHER PUBLICATIONS

Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/USO4/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 10 185386.9 dated Jan. 10, 2011.
Int'l Search Report EP 10 185405.7 dated Jan. 5, 2011.
Int'l Search Report EP 11 168419.7 dated Oct. 20, 2011.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

(56) References Cited

OTHER PUBLICATIONS

Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
International Search Report PCT/US2012/049928 dated Jan. 21, 2013.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 186527.7 dated Jun. 17, 2011.
Int'l Search Report Ep 10 189206.5 dated Mar. 17, 2011.
Int'l Search Report EP 10 191320.0 dated Feb. 15, 2011.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
In'tl Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.

* cited by examiner

SURGICAL FORCEPS

BACKGROUND

1. Technical Field

The present disclosure relates to surgical instruments and, more particularly, to surgical forceps for grasping, sealing and/or dividing tissue.

2. Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

Generally, surgical instruments, including forceps, can be classified as single-use instruments, e.g., instruments that are discarded after a single use, partially-reusable instruments, e.g., instruments including both disposable portions and portions that are sterilizable for reuse, and completely reusable instruments, e.g., instruments that are completely sterilizable for repeated use. As can be appreciated, those instruments (or components of instruments) that can be sterilized and reused help reduce the costs associated with the particular surgical procedure for which they are used. However, although reusable surgical instruments are cost-effective, it is important that these instruments be capable of performing the same functions as their disposable counterparts and that any disposable components of these instruments be efficiently removable and replaceable with new components.

SUMMARY

In accordance with one embodiment of the present disclosure, a forceps is provided. The forceps includes a disposable shaft member and a reusable shaft member. The shaft members each include a jaw member disposed at the distal end thereof. The shaft members are releasably coupled to one another about a pivot and are moveable relative to one another between, e.g., between a spaced-apart position and an approximated position, for moving the jaw members between an open position and a closed position for grasping tissue therebetween. The disposable shaft member includes a first electrically-conductive tissue sealing plate disposed on the jaw member thereof. An electrical connector is coupled to the disposable shaft member. The electrical connector is adapted to connect to a source of energy and includes a plurality of wires extending therethrough and into the disposable shaft member. One or more of the wires extend through the disposable shaft member to electrically couple to the first electrically-conductive tissue sealing plate and one or more of the wires extend through the disposable shaft member and therefrom to couple to a second electrically-conductive tissue sealing plate that is configured for releasable engagement with the jaw member of the reusable shaft member. The electrically-conductive tissue sealing plates are adapted to conduct energy, e.g., from the source of energy via the wires, through tissue for sealing tissue grasped between the jaw members.

In one embodiment, the disposable shaft member includes a knife assembly disposed therein. The knife assembly includes a knife blade that is translatable between a retracted position, wherein the knife blade is disposed within the disposable shaft member, and an extended position, wherein the knife blade extends between the jaw members to cut tissue grasped therebetween.

In another embodiment, a trigger assembly is operably coupled to the disposable shaft member. The trigger assembly includes a trigger extending from the disposable shaft member that is selectively movable between a first position and a second position to translate the knife blade between the retracted position and the extended position.

In yet another embodiment, the disposable shaft member further includes an activation assembly operably coupled to one or more of the wires extending therethrough. The activation assembly includes an activation switch operably coupled to the disposable shaft member that is selectively actuatable to supply energy to the electrically conductive tissue sealing plates.

In still another embodiment, the second electrically-conductive tissue sealing plate is disposed on an insulative component. The insulative component, in turn, is configured to releasably engage a jaw frame of the jaw member of the reusable shaft such that the jaw frame of the reusable shaft and the second electrically-conductive tissue sealing plate are electrically insulated from one another.

Another embodiment of a forceps provided in accordance with the present disclosure includes first and second shaft members, each of which includes a jaw member disposed at a distal end thereof. The shaft members are releasably coupled to one another about a pivot pin and are moveable relative to one another, e.g., between a spaced-apart position and an approximated position, for moving the jaw members between an open position and a closed position for grasping tissue therebetween. One or both of the shaft members includes an aperture defined transversely therethrough that is configured to receive the pivot pin therethrough for coupling the first and second shaft members to one another. The pivot pin includes a hub disposed at a first end thereof and a pair of legs extending from the hub. The legs are coupled to one another via a living hinge and are biased towards a spaced-apart position. Each of the legs includes an outwardly-extending tab disposed at the free end thereof. The legs are moveable relative to one another from the spaced-apart position to a closer position for insertion of the pivot pin through the aperture(s) of the shaft member(s). Once inserted through the aperture of the shaft member, the legs are biased back towards the spaced-apart position such that the pivot pin pivotably engages the shaft members to one another between the hub and the outwardly-extending tabs thereof.

In one embodiment, the pivot pin is fixedly engaged to one of the shaft members. Alternatively, the pivot pin may be removably insertable through apertures defined within each of the shaft members.

In another embodiment, one of the shaft members is disposable and the other shaft member is reusable. The disposable shaft member may include a knife assembly, trigger assembly, and/or an activation assembly, similarly as described in the previous embodiments.

Still another embodiment of a forceps provided in accordance with the present disclosure includes first and second shaft members, each of which includes a jaw member disposed at a distal end thereof. The shaft members are removably coupled to one another about a pivot pin. One or both of the shaft members includes an aperture extending transversely therethrough that is shaped complementarily to the pivot pin and is configured to receive the pivot pin therethrough. The shaft members are moveable relative to one another between an unlocked position, wherein the aperture(s) is oriented to permit insertion of the pivot pin therethrough and removal of the pivot pin therefrom for engaging and disengaging, respectively, the shaft members from one another, and a locked position, wherein the aperture(s) is oriented to inhibit removal of the pivot pin therefrom to lock the shaft members in pivotable engagement with one another. In the locked position, the shaft members are moveable relative to one another for moving the jaw members between an open position and a closed position for grasping tissue therebetween.

In one embodiment, in the unlocked position, the shaft members are disposed in substantially transverse relation relative to one another. The forceps may otherwise be configured similarly to any of the embodiments above.

BRIEF DESCRIPTION OF THE DRAWINGS

Various embodiments of the present disclosure are described herein with reference to the drawings wherein.

DETAILED DESCRIPTION

Figure 1A:
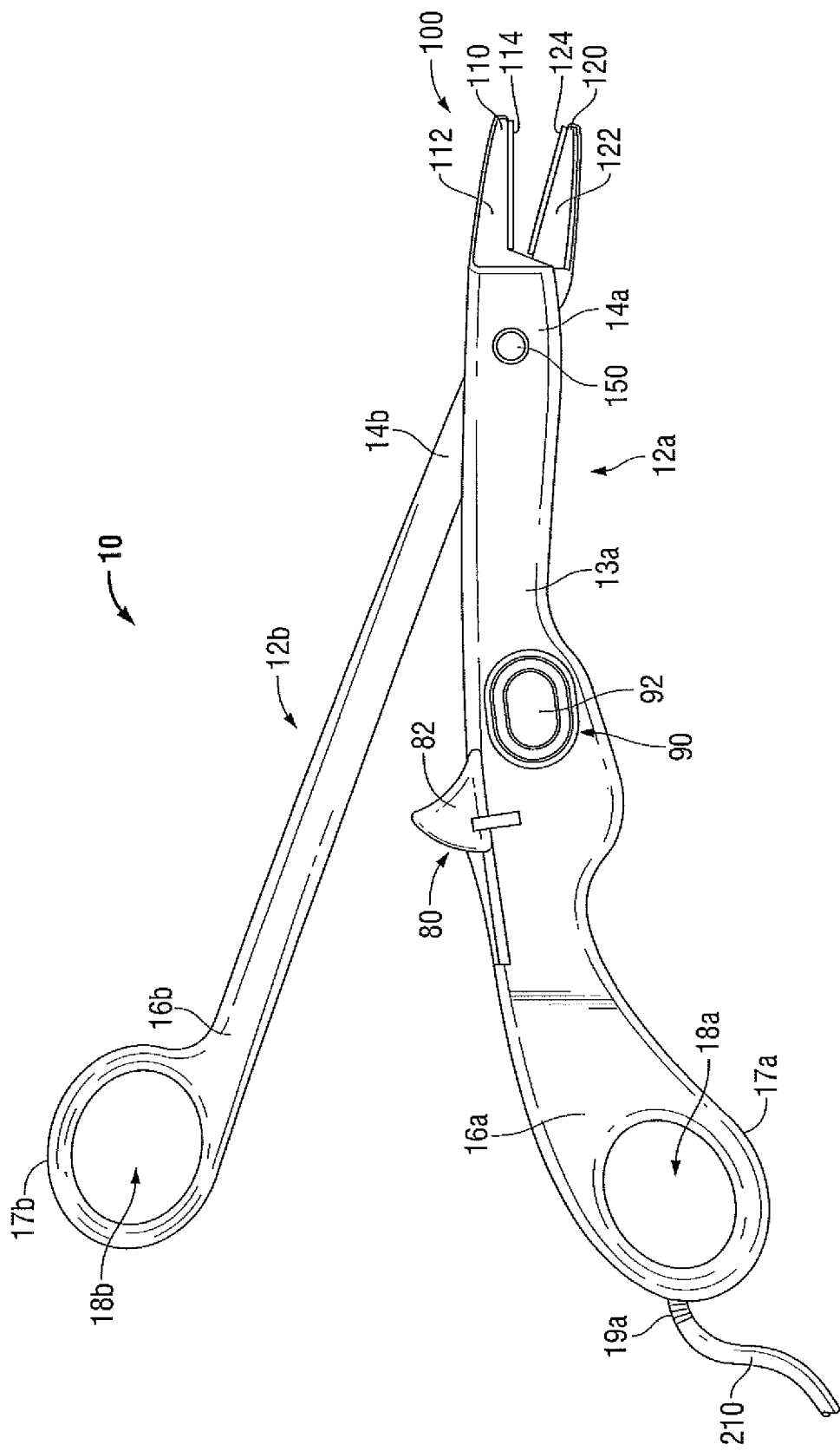
FIG. 1A is a side view of a forceps provided in accordance with one embodiment of the present disclosure wherein jaw members of the forceps are disposed in an open configuration.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1B:
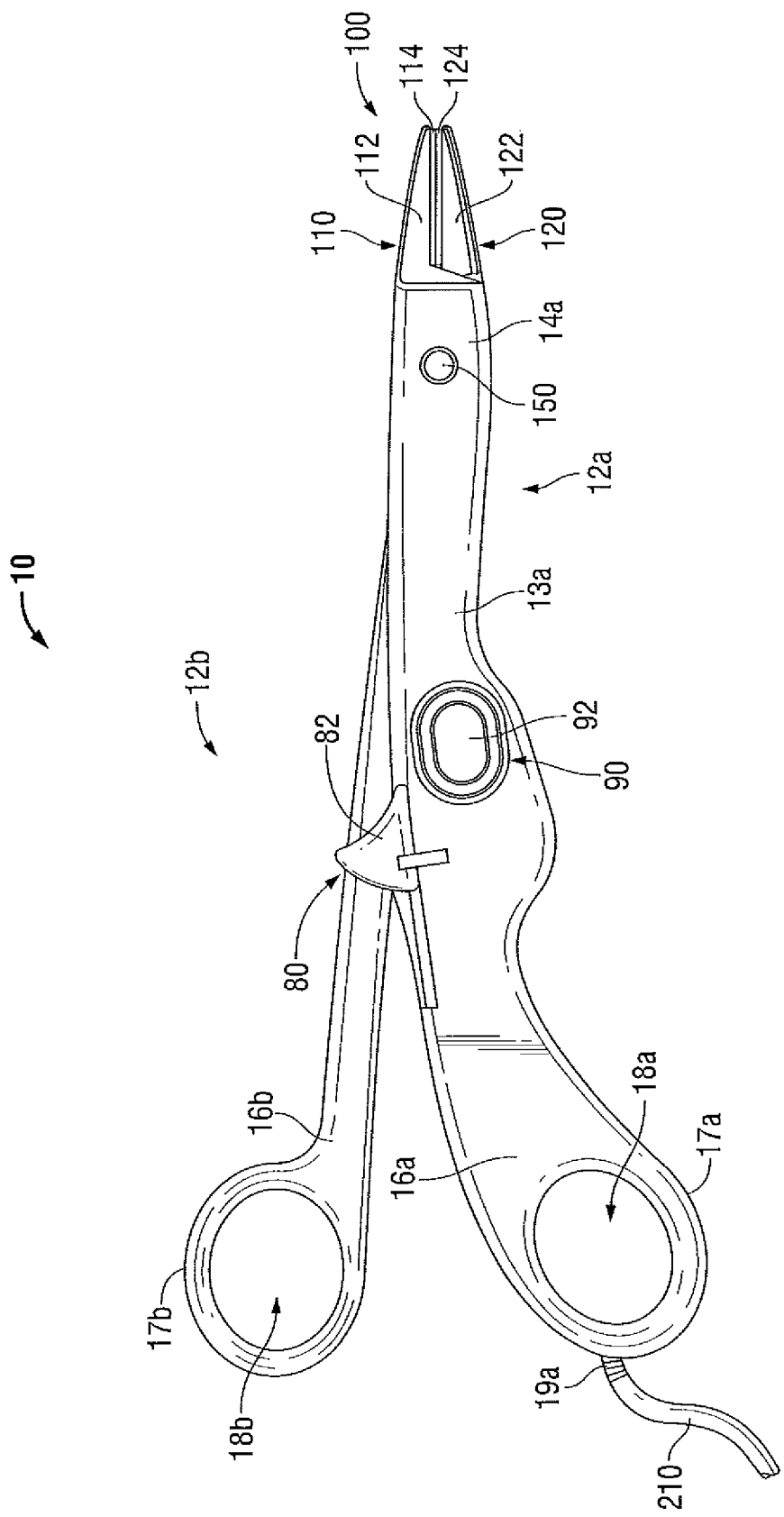
FIG. 1B is a side view of the forceps of FIG. 1A wherein the jaw members are disposed in a closed configuration.

Referring initially to FIGS. 1A and 1B, a forceps 10 is shown including two elongated shaft members 12a and 12b each having a distal end 14a and 14b and a proximal end 16a and 16b, respectively. End effector assembly 100, including opposing jaw members 110, 120, is attached to distal ends 14a and 14b of shaft members 12a and 12b, respectively. A pivot pin 150 is interdisposed between shaft members 12a, 12b and the respective jaw members 110, 120 thereof such that shaft members 12a, 12b may be pivoted relative to one another between a spaced-apart position (FIG. 1A) and an approximated position (FIG. 1B) to effect movement of jaw members 110, 120 relative to one another between an open position (FIG. 1A) and a closed position (FIG. 1B), respectively, for grasping tissue therebetween.

Jaw members 110, 120 of end effector assembly 100 each include a jaw frame 112, 122 that is fixedly engaged to the respective shaft member 12a, 12b and an opposed electrically-conductive tissue sealing plate 114, 124, respectively, disposed on the respective jaw frame 112, 122. One or both of electrically-conductive tissue sealing plates 114, 124 of jaw members 110, 120, respectively, are adapted to connect to a source of electrosurgical energy for conducting energy through tissue to seal tissue grasped between jaw members 110, 120.

With continued reference to FIGS. 1A and 1B, each shaft member 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of shaft members 12a and 12b relative to one another between the spaced-apart and approximated positions which, in turn, pivots jaw members 110 and 120 between the open position (FIG. 1A) and the closed position (FIG. 1B).

Shaft members 12a, 12b are releasably coupled to one another, e.g., via decoupling one or both of shaft members 12a, 12b from pivot pin 150, such that one of the shaft members, e.g., shaft member 12a, may be disposed of and replaced with a new shaft member 12a, while the other shaft member, e.g., shaft member 12b, may be sterilized and/or otherwise treated in preparation for re-use. Accordingly, as will be described in greater detail below, each of the shaft members 12a, 12b includes different components and features suitable for the specific configuration, e.g., disposable or reusable, of the shaft member 12a, 12b.

Figure 2:
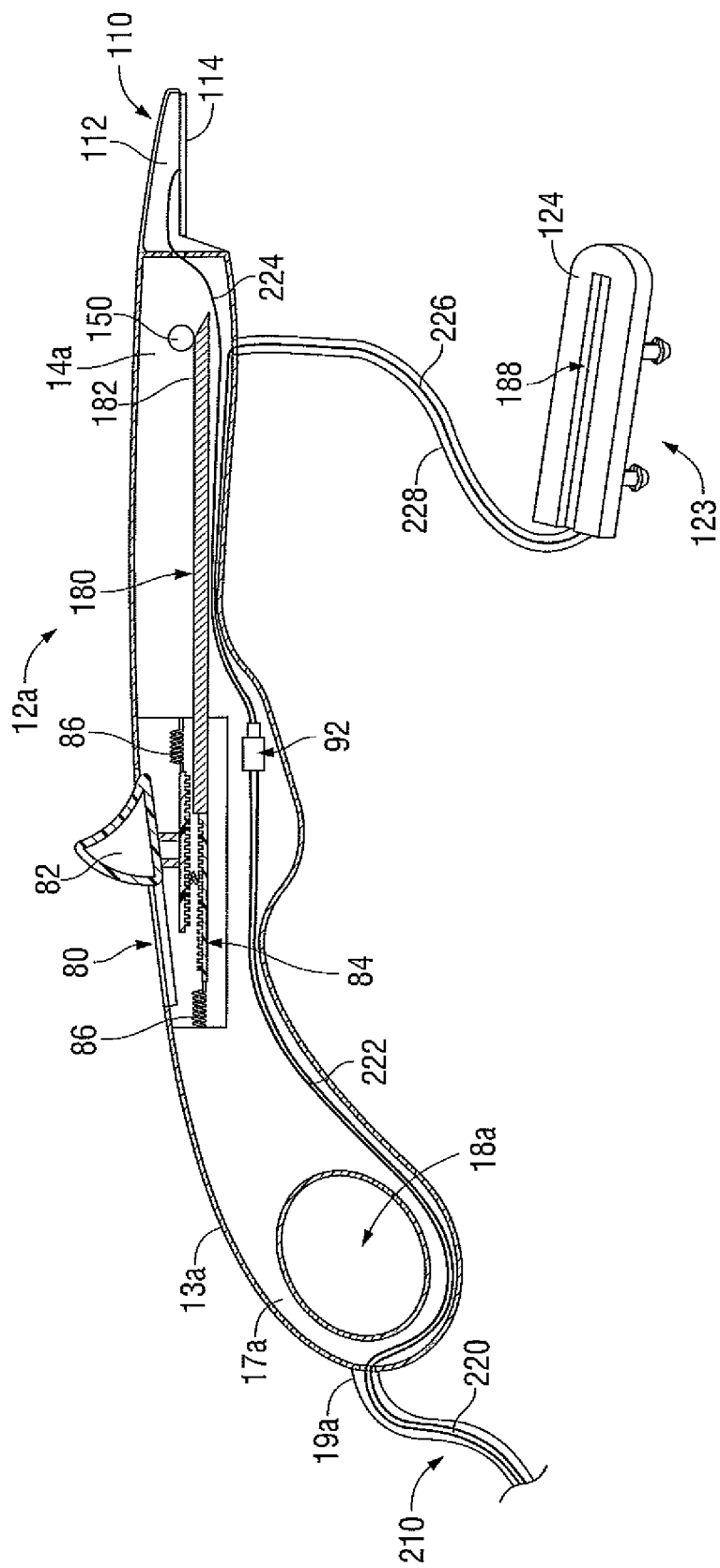
FIG. 2 is a side, cross-sectional view of one of the shaft members of the forceps of FIG. 1A.

Referring now to FIG. 2, in conjunction with FIGS. 1A-1B, shaft member 12a is shown. Shaft member 12a is configured as a disposable component that is to be disposed of and replaced with a new disposable shaft member 12a after each use, or each surgical procedure. Shaft member 12a includes an outer housing 13a that may be formed from plastic or other suitable material. Outer housing 13a houses the internal working components of shaft member 12a. Shaft member 12a further includes an aperture 160 (FIGS. 5A-5B) extending transversely therethrough adjacent distal end 14a thereof that is configured to receive pivot pin 150 therethrough for pivotably coupling shaft member 12 and shaft member 12b to one another. Pivot pin 150 may be removably coupled within aperture 160 (FIGS. 5A-5B) defined through shaft member 12a, or may be fixedly secured therein for releasable coupling with shaft member 12b to permit pivoting of shaft member 12b relative to shaft member 12a and pivot pin 150 from the spaced-apart position (FIG. 1A) to the approximated position (FIG. 1B) for moving jaw members 110, 120 between the open and closed positions, respectively.

A proximal shaft connector 19a extends proximally from outer housing 13a of shaft member 12a. Proximal shaft connector 19a is designed to connect the forceps 10 to a source of electrosurgical energy such as an electrosurgical generator (not shown). More specifically, proximal shaft connector 19a secures an electrosurgical cable 210 to the forceps 10 such that the user may selectively apply electrosurgical energy to tissue sealing plates 114, 124 of jaw members 110, 120, respectively, e.g., via actuation of activation switch 92 of activation assembly 90 (see FIG. 1A), to seal tissue grasped therebetween.

Electrosurgical cable 210 includes one or more wires 220, 222 extending therethrough that extend into outer housing 13a of shaft member 12a. One more wires 220, 222 extends through shaft member 12a, ultimately coupling to activation assembly 90. Further one or more wires, e.g., wire 224, extends from activation assembly 90 (and/or electrosurgical cable 210), ultimately coupling to tissue sealing plates 114 of jaw members 110, while another wire, e.g., wire 226, extends from activation assembly 90 through shaft member 12a and outer of shaft member 12a towards distal end 14a thereof, ultimately coupling to tissue sealing plate 124 of removable component 123 of jaw member 120. Wire 226 may include an insulative coating, or sleeve 228 disposed thereabout such that wire 226 is insulated when disposed externally of shaft member 12a. Further, shaft member 12a (and/or shaft member 12b) may include clips, grooves, or other suitable mechanisms (not explicitly shown) for routing wire 226 along the external surface(s) of shaft member(s) 12a, 12b such that wire 226 does not interfere with the use and operation of forceps 10 and such that wire 226 does not catch or tangle during use of forceps 10. As will be described below, disposable component 123 of jaw member 120 is configured to engage jaw frame 122 of jaw member 120 of reusable shaft 12b. As such, the user may selectively actuate activation switch 92 of activation assembly 90 to supply energy to tissue sealing plates 114, 124 of jaw members 110, 120, respectively, for sealing tissue grasped therebetween.

Continuing with reference to FIG. 2, in conjunction with FIGS. 1A and 1B, shaft member 12a further includes a knife assembly 180 disposed therein and a trigger assembly 80 coupled thereto. Trigger assembly 80 includes a trigger 82 that is selectively translatable between first and second positions to advance knife blade 182 (FIG. 3) from a retracted position, wherein knife blade 182 is disposed within shaft member 12a, and an extended position, wherein knife blade 182 extends between jaw members 110, 120 to cut tissue grasped therebetween. As shown in FIG. 2, trigger assembly 80 includes a gear mechanism 84 biased by springs 86 for selectively translating knife blade 182 from the retracted position to the extended position upon movement of trigger 82 proximally from the first position to the second position. Springs 86 bias trigger 82 distally toward the first position and, accordingly, bias knife blade 182 toward the retracted position. However, other trigger assemblies 80 and/or knife assemblies 180 may also be provided for use in conjunction with shaft member 12a, such as those disclosed in commonly-owned U.S. Pat. No. 7,131,970 to Moses et al.

One or both of tissue sealing plates 114, 124 of jaw members 110, 120, respectively, may include a blade slot 188 (FIGS. 2-3) defined therein and extending therethrough. Blade slot 188 is configured to permit reciprocation of knife blade 182 therethrough. Blade slot 188 may be defined completely within one of the jaw members, e.g., jaw member 120, or may be formed partially within each of the jaw members 110, 120 such that blade slot 188 is formed as jaw members 110 and 120 come together upon pivoting of the jaw members 110 and 120 to the closed position. Further, the blade slot 188 may be configured to facilitate and/or enhance cutting of tissue during reciprocation of the knife blade 182 therethrough.

Figure 3:
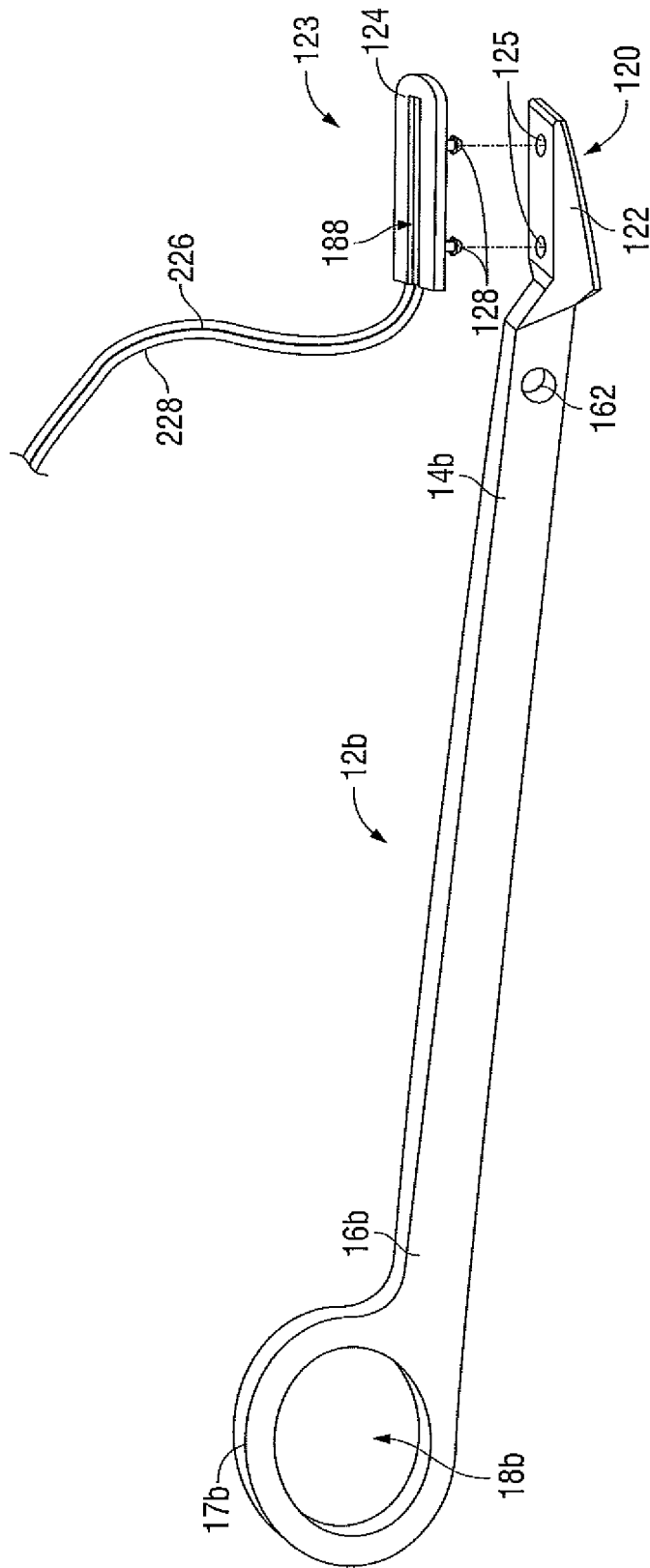
FIG. 3 is an exploded, side, perspective view of the other shaft member of the forceps of FIG. 1A.

Turning now to FIG. 3, in conjunction with FIGS. 1A and 1B, reusable shaft member 12b is shown. Shaft member 12b may be formed form any suitable material, e.g., stainless steel, capable of being sterilized, e.g., placed in an autoclave (not shown), or otherwise prepared for reuse. Shaft member 12b further includes an aperture 162 defined therein and extending transversely therethrough towards distal end 14b thereof that is configured to receive pivot pin 150 therethrough for releasably coupling shaft members 12a and 12b to one another. Shaft member 12b may define a partially or entirely solid interior configuration to achieve greater strength and/or may otherwise be configured for increased durability such that shaft member 12b can be used repeatedly without significant wearing. As mentioned above, shaft member 12b includes jaw frame 122 of jaw member 120 disposed at distal end 14b thereof. Jaw frame 122 includes a pair of apertures 125 configured to receive snap-fit protrusions 128 of disposable component 123 for releasably securing disposable component 123 thereon, e.g., in snap-fit engagement therewith, although other releasable engagement configurations are contemplated. Disposable component 123 includes electrically-conductive tissue sealing plate 124 disposed about an insulative member (not explicitly shown). Snap-fit protrusions 128 extend from the insulative member (not explicitly shown). Accordingly, when disposable component 123 is engaged to jaw frame 122, the insulative member (not explicitly shown) is interdisposed between tissue sealing plate 124 and jaw frame 122, insulating jaw frame 122 from tissue sealing plate 124. As mentioned above, tissue sealing plate 124 of disposable component 123 is coupled to the source of energy (not shown) via wire(s) 226 such that jaw member 120, in conjunction with jaw member 110 may be used to conduct energy through tissue grasped therebetween to seal tissue.

Reusable shaft member 12b defines a relatively simplified, strong, and durable configuration that facilitates sterilization and repeated use of shaft member 12b, while disposable shaft member 12a includes activation assembly 90, trigger assembly 80, knife assembly 180, and the various components and connections associated therewith. Including these various components with shaft member 12a allows new components to be used for each surgical procedure, obviating the need to make these components sterilizable or configured for long-term repeated use. Further, tissue sealing plate 114 of jaw member 110 of disposable shaft 12a, and tissue sealing plate 124 of disposable component 123 of jaw member 120 are also configured as disposable components such that a new set of tissue sealing plates 114, 124 may be used for each procedure. Various configurations for releasably engaging disposable shaft 12a and reusable shaft 12b to one another about pivot pin 150 are described below. Each of these configurations facilitates disengagement of shaft members 12a, 12b such that shaft member 12a may be discarded and such that shaft member 12b may be sterilized for reuse and facilitates engagement of shaft member 12b with a new shaft member 12a in preparation for subsequent use.

Figure 4A:
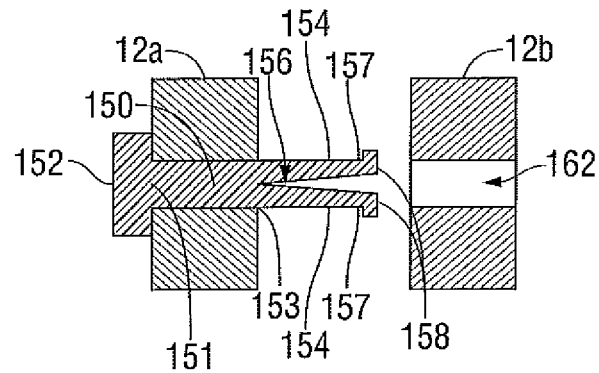
FIG. 4A is transverse, cross-sectional view of one embodiment of shaft members configured for use with the forceps of FIG. 1A, wherein the shaft members are disengaged from one another.
Figure 4B:
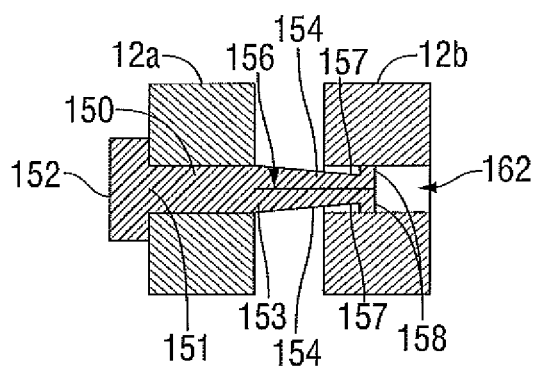
FIG. 4B is a transverse, cross-sectional view of the shaft members of FIG. 4A during engagement to one another via a pivot pin extending from one of the shaft members.
Figure 4C:
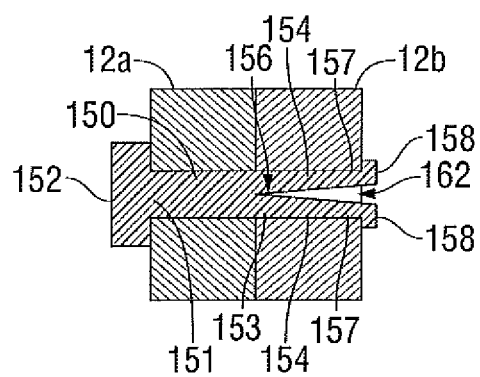
FIG. 4C is a transverse, cross-sectional view of the shaft members of FIG. 4A engaged to one another via the pivot pin.

Referring now to FIGS. 4A-4C, pivot pin 150 is shown fixedly engaged through shaft member 12a. Pivot pin 150 further includes a hub 152 disposed at first end 151 thereof and a pair of adjacent legs 154 disposed at second end 153 thereof. Legs 154 extend from pivot pin 150 and define a living hinge 156 therewith. More specifically, legs 154 are biased towards a spaced-apart position relative to one another, but are moveable against the bias of living hinge 156 toward an approximated position wherein legs 154 are abutting, or disposed in close relation relative to one another to facilitate insertion of pivot pin 150 through aperture 162 of shaft member 12b. Legs 154 each further include an outwardly-extending tab 158 disposed at the free ends 157 thereof.

Continuing with reference to FIGS. 4A-4C, in order to couple shaft members 12a and 12b to one another, shaft members 12a, 12b are brought into approximation with one another such that pivot pin 150 is inserted through aperture 162 of shaft member 12b. More specifically, legs 154 of pivot pin 150 and, thus, tabs 158 thereof, are urged, or squeezed toward one another such that pivot pin 150 may be advanced through aperture 162 of shaft member 12b, as shown in FIG. 4B. As tabs 158 extend from aperture 162 on the other side thereof, legs 154 are permitted to return under the bias of living hinge 156 back toward the spaced-apart position. In this position, as shown in FIG. 4C, tabs 158 extend radially outwardly from aperture 162 about shaft member 12b to inhibit backing out of pivot pin 150, thus pivotably engaging shaft members 12a and 12b to one another, while still permitting shaft member 12b to rotate about pivot pin 150 and relative to shaft member 12a. In order to disengage shaft member 12b from shaft member 12a and pivot pin 150, tabs 158 are urged, or squeezed toward one another a sufficient distance such that legs 154 may pass back through aperture 162 of shaft member 12b.

Figure 5A:
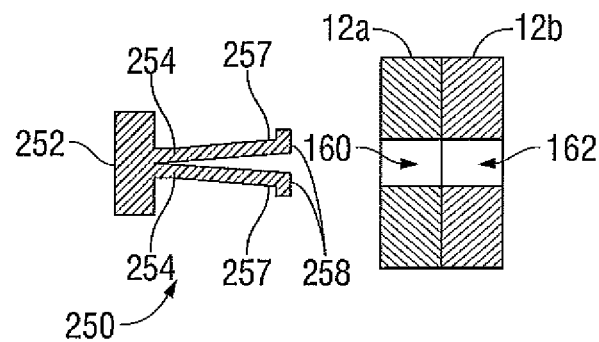
FIG. 5A is transverse, cross-sectional view of another embodiment of shaft members configured for use with the forceps of FIG. 1A, wherein the shaft members are disengaged from one another.
Figure 5B:
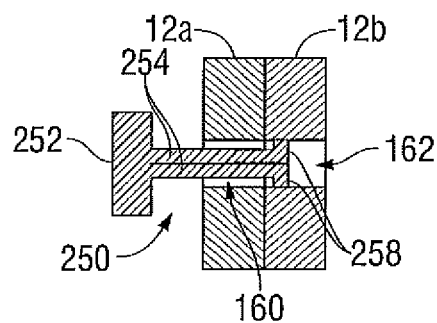
FIG. 5B is a transverse, cross-sectional view of the shaft members of FIG. 5A shown including a pivot pin being inserted therethrough to engage the shaft members to one another.
Figure 5C:
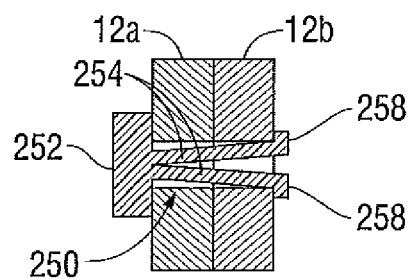
FIG. 5C is a transverse, cross-sectional view of the shaft members of FIG. 5A shown engaged to one another via the pivot pin.

FIGS. 5A-5C show another embodiment of a pivot pin 250 similar to pivot pin 150 (FIGS. 4A-4C) except that pivot pin 250 is releasably engagable with both shaft member 12a and shaft member 12b. Further, as opposed to legs 154 (FIGS. 4A-4C) of pivot pin 150 (FIGS. 4A-4C), living-hinge legs 254 of pivot pin 250 extend directly from hub 252 to free ends 257 thereof, i.e., legs 254 extend along the length of pivot pin 250, although either of pivot pins 150, 250 may be used in conjunction with the configurations of FIGS. 4A-4C and 5A-5C.

In use, legs 254 of pivot pin 250 and, thus, tabs 258 thereof, are urged, or squeezed toward one another such that pivot pin 250 may be advanced through aperture 160 defined within shaft member 12a and aperture 262 of shaft member 12b. Ultimately, pivot pin 250 is advanced through shaft members 12a, 12b until tabs 258 extend from aperture 262 on the other side thereof. Once this position is achieved, legs 254 are permitted to return under the bias of living hinge 256 back toward the spaced-apart position. In this position, as shown in FIG. 5C, tabs 258 extend radially outwardly from aperture 262 about shaft member 12b to inhibit backing out of pivot pin 250, while hub 252 of pivot pin 250 inhibits further advancement of pivot pin 250 through aperture 260 shaft member 12a. Accordingly, shaft members 12a and 12b are pivotably engaged to one another, while still permitting shaft members 12a and 12b to rotate about pivot pin 150 relative to one another. Pivot pin 250 is disengaged from shaft members 12a, 12b similarly as described above with respect to pivot pin 150 (FIGS. 4A-4C).

Figure 6B:
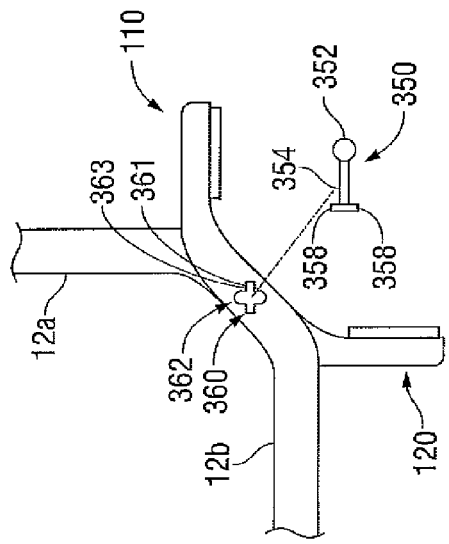
FIG. 6B is a side view of the shaft members of FIG. 6A shown in an unlocked position for engaging and/or disengaging the shaft members to one another.
Figure 6C:
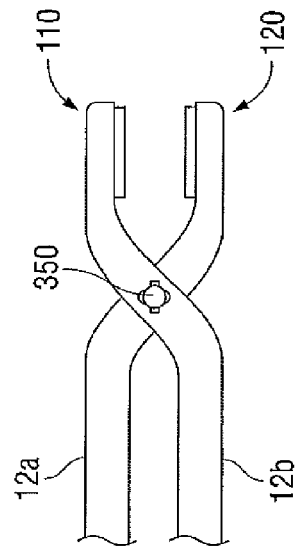
FIG. 6C is a side view of the shaft members of FIG. 6A shown in a locked position.
Figure 6A:
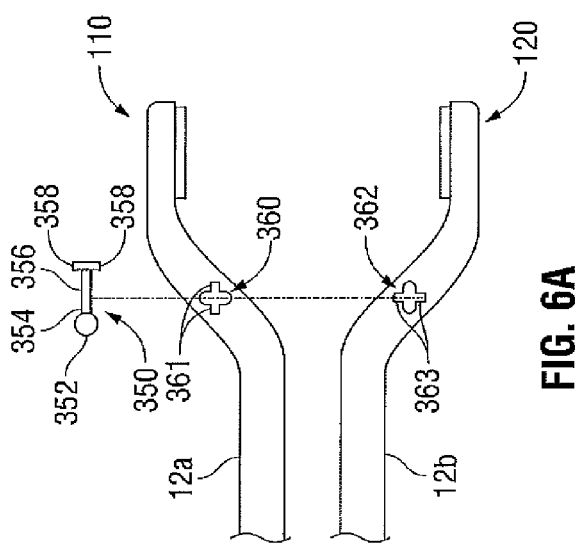
FIG. 6A is an exploded, side view of another embodiment of shaft members configured for use with the forceps of FIG. 1A.

Referring now to FIGS. 6A-6C, another configuration for engaging shaft members 12a, 12b to one another is shown. In this embodiment, pivot pin 350 defines a key-like configuration having a hub 352, an elongated member 354 extending therefrom, and a pair of opposed tabs 358 extending radially outwardly from elongated member 354 at free end 356 thereof. Shaft members 12a, 12b define apertures 360, 362, respectively, extending transversely therethrough that are shaped complementarily to pivot pin 350 such that pivot pin 350 may be inserted therethrough. More specifically, shaft members 12a, 12b each define a generally circular-shaped aperture 360, 362 having a pair of opposed recessed portions 361, 363, respectively, defined therein for receiving tabs 358 of pivot pin 350 therethrough. However, as shown in FIG. 6C, apertures 360, 362 disposed on shaft members 12a, 12b, respectively, are offset approximately 90 degrees relative to one another. Accordingly, shaft members 12a, 12b must be oriented substantially perpendicularly to one another (the unlocked position), as shown in FIG. 6B, such that apertures 360, 362 are aligned with one another to permit insertion (or removal) of pivot pin 350 therethrough.

Referring now to FIGS. 6B-6C, and initially to FIG. 6B, in use, shaft members 12a, 12b are positioned substantially perpendicularly to one another such that apertures 360, 362 are aligned with one another. In this unlocked position, pivot pin 350 may be inserted through apertures 360, 362. More specifically, tabs 358 of pivot pin 350 are advanced through recessed portions 361 of aperture 360 of shaft member 12a and through recessed portions 363 of aperture 362 of shaft member 12b such that tabs 358 extend from aperture 362 of shaft member 12b on the other side thereof. Once pivot pin 350 has been inserted through shaft members 12a, 12b, shaft member 12b may be rotated about pivot pin 350 and relative to shaft member 12a from the unlocked position to the locked position, e.g., the spaced-part position, the approximated position, or any position therebetween, as shown in FIG. 5C. In this locked position, shaft members 12a, 12b are locked in engagement with one another in that pivot pin 350 is inhibited from backing out of aperture 362 of shaft member 12b due to the offset alignment of tabs 358 relative to recessed portions 363, and is inhibited from advancing further through aperture 361 of shaft member 12a due to hub 352 thereof. However, in this locked position, shaft members 12a, 12b are still permitted to pivot about pivot pin 350 and relative to one another between the spaced-apart position and the approximated position. As can be appreciated, in order to disengage shaft members 12a, 12b from one another, shaft members 12a, 12b are once again moved to the unlocked position, wherein shaft members 12a, 12b are positioned substantially perpendicularly relative to one another, thus allowing pivot pin 350 to be removed therefrom. Accordingly, shaft member 12b may then be sterilized for reuse, while shaft member 12a is disposed of and a new shaft member 12a is provided for coupling to shaft member 12b in preparation for reuse.

Figure 7A:
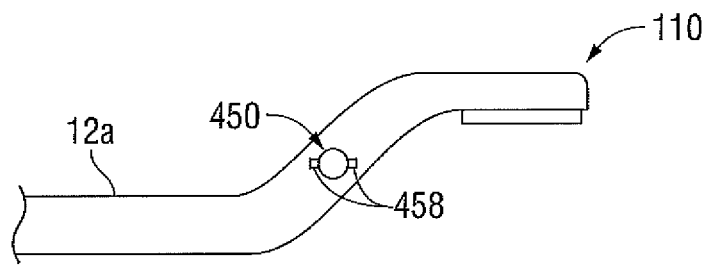
FIG. 7A is a side view of another embodiment of a shaft member including an engagement pin extending therefrom.
Figure 7B:
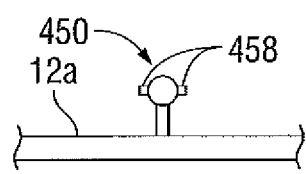
FIG. 7B is top view of the shaft member of FIG. 7A.
Figure 7C:
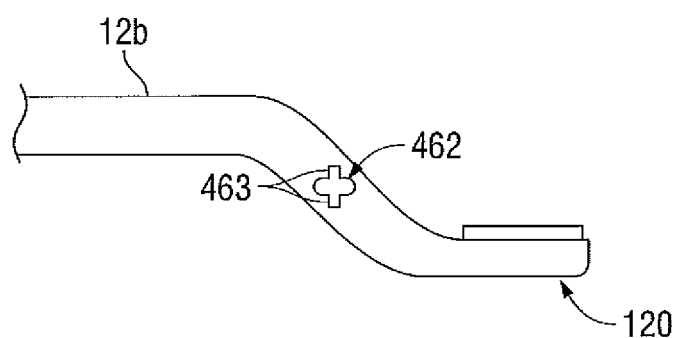
FIG. 7C is a side view of a shaft member including an engagement aperture configured to receive the engagement pin of the shaft member of FIG. 7A to engage the shaft members to one another.

With reference now to FIGS. 7A-7C, another configuration for engaging shaft members 12a, 12b to one another is shown that is substantially similar to the configuration shown in FIGS. 6A-6C except that pivot pin 450 is fixedly secured to shaft member 12a and extends transversely therefrom. The engagement and disengagement of shaft 12a and 12b is substantially similar as described above with respect to FIGS. 6A-6C and, thus, will only be summarized herein for purposes of brevity.

In use, shaft members 12a, 12b are positioned substantially perpendicularly to one another such that tabs 458 of pivot pin 450 of shaft member 12a are aligned with recessed portions 463 of aperture 462 of shaft member 12b. In this unlocked position, pivot pin 450 may be advanced through aperture 462 to extend therefrom on the other side thereof. Once this position has been achieved, shaft member 12b may be rotated about pivot pin 450 and relative to shaft member 12a from the unlocked position to the locked position. In this locked position, tabs 458 of pivot pin 450 of shaft member 12 are no longer aligned with recessed portions 463 of aperture 462 of shaft member 12b, thereby locking shaft members 12a, 12b in engagement with one another while still permitting shaft member 12b to be pivoted about pivot pin 450 and relative to shaft member 12a between the spaced-apart position and the approximated position. Disengagement of shaft members 12a, 12b, on the other hand, is accomplished by returning shaft member 12b to the substantially perpendicular position relative to shaft member 12a such that pivot pin 450 may be translated back through aperture 462.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    a disposable shaft member and a reusable shaft member, the shaft members each including a jaw member disposed at a distal end thereof, the shaft members selectively replaceable with respect to one another wherein, when engaged with one another, the shaft members are movable relative to one another about a pivot for moving the jaw members between an open position and a closed position for grasping tissue therebetween, the disposable shaft member including:
    a first electrically-conductive tissue sealing plate permanently disposed on the jaw member of the disposable shaft member;
    an electrical connector coupled to the disposable shaft member, the electrical connector adapted to connect to a source of energy and including a plurality of wires extending therethrough and into the disposable shaft member, at least one first wire electrically coupled to the first electrically-conductive tissue sealing plate for enabling energy to be supplied thereto;
    a second electrically-conductive tissue sealing plate selectively replaceable with respect to the jaw member of the reusable shaft member; and
    at least one second wire of the plurality of wires electrically coupled to the second electrically-conductive tissue sealing plate to both permanently couple the second electrically-conductive tissue sealing plate with the disposable shaft member and enable energy to be supplied thereto.

2. The forceps according to claim 1, wherein the disposable shaft member further includes a knife assembly disposed therein, the knife assembly including a knife blade translatable between a retracted position, wherein the knife blade is disposed within the disposable shaft member, and an extended position, wherein the knife blade extends between the jaw members to cut tissue grasped therebetween.

3. The forceps according to claim 2, further comprising a trigger assembly operably coupled to the disposable shaft member, the trigger assembly including a trigger extending from the disposable shaft member that is selectively movable between a first position and a second position to translate the knife blade between the retracted position and the extended position.

4. The forceps according to claim 1, wherein the disposable shaft member further includes an activation assembly operably coupled to at least one of the plurality of wires extending through the disposable shaft member, the activation assembly including an activation switch operably coupled to the disposable shaft member that is selectively actuatable to supply energy to the electrically conductive tissue sealing plates.

5. The forceps according to claim 1, wherein the second electrically-conductive tissue sealing plate is disposed on an insulative component, the insulative component selectively replaceable with respect to the jaw member of the reusable shaft such that the reusable shaft and the second electrically-conductive tissue sealing plate are electrically insulated from one another.

6. The forceps according to claim 1, wherein at least one of the shaft members includes an aperture defined transversely therethrough for insertion of a pivot pin therethrough for coupling the first and second shaft members to one another, the pivot pin including:
    a hub disposed at a first end of the pivot pin;
    a pair of legs extending from the hub, the legs coupled to one another via a living hinge and biased towards a spaced-apart position, each of the legs including an outwardly-extending tab disposed at the free end thereof, the legs moveable relative to one another from the spaced-apart position to a closer position for insertion of the pivot pin through the aperture of the at least one shaft member, the legs biased back towards the spaced-apart position upon passage of the tabs through the at least one aperture such that the pivot pin pivotably engages the shaft members to one another between the hub and the outwardly-extending tabs thereof.

7. The forceps according to claim 6, wherein the pivot pin is fixedly engaged to one of the first and second shaft members.

8. The forceps according to claim 6, wherein the pivot pin is removably insertable through apertures defined within each of the shaft members for removably engaging the first and second shaft members to one another.

9. The forceps according to claim 1, wherein at least one of the shaft members includes an aperture extending transversely therethrough that is shaped complementarily to a pivot pin and is configured to receive the pivot pin therethrough, the shaft members moveable relative to one another between an unlocked position, wherein the at least one aperture is oriented to permit insertion of the pivot pin therethrough and removal of the pivot pin therefrom for engaging and disengaging, respectively, the shaft members from one another, and a locked position, wherein the at least one aperture is oriented to inhibit removal of the pivot pin therefrom to lock the shaft members in pivotable engagement with one another, wherein, in the locked position, the shaft members are moveable relative to one another for moving the jaw members between the open position and the closed position.

10. The forceps according to claim 9, wherein, in the unlocked position, the shaft members are disposed in substantially transverse relation relative to one another.

11. The forceps according to claim 9, wherein the pivot pin is fixedly engaged to one of the first and second shaft members.

12. The forceps according to claim 9, wherein the pivot pin is removably insertable through apertures defined within each of the shaft members for removably engaging the first and second shaft members to one another.

\* \* \* \* \*